United States Patent
Tarkin-Tas et al.

(10) Patent No.: US 10,995,182 B2
(45) Date of Patent: May 4, 2021

(54) PHENYLENE ETHER OLIGOMER, CURABLE COMPOSITION COMPRISING THE PHENYLENE ETHER OLIGOMER, AND THERMOSET COMPOSITION DERIVED THEREFROM

(71) Applicant: SABIC GLOBAL TECHNOLOGIES B.V., Bergen op Zoom (NL)

(72) Inventors: Eylem Tarkin-Tas, Delmar, NY (US); Huseyin Tas, Delmar, NY (US)

(73) Assignee: SHPP GLOBAL TECHNOLOGIES B.V., Bergen op Zoom (NL)

( * ) Notice: Subject to any disclaimer, the term of this patent is extended or adjusted under 35 U.S.C. 154(b) by 141 days.

(21) Appl. No.: 16/377,935

(22) Filed: Apr. 8, 2019

(65) Prior Publication Data
US 2019/0330424 A1    Oct. 31, 2019

(30) Foreign Application Priority Data
Apr. 30, 2018 (EP) .................................... 18170027

(51) Int. Cl.
  C08G 81/02    (2006.01)
  C07C 39/17    (2006.01)
  C08G 65/40    (2006.01)

(52) U.S. Cl.
  CPC ............ C08G 81/025 (2013.01); C07C 39/17 (2013.01); C08G 65/4087 (2013.01)

(58) Field of Classification Search
  CPC ..... C08F 20/06; C07D 303/12; C08G 81/025; C08G 65/4087; C07C 39/17
  See application file for complete search history.

(56) References Cited

U.S. PATENT DOCUMENTS

| | | | |
|---|---|---|---|
| 3,018,290 A | 1/1962 | Sauers et al. | |
| 3,205,271 A * | 9/1965 | Ecke | C07C 39/17 568/744 |
| 3,562,223 A | 2/1971 | Bargain et al. | |
| 4,211,860 A | 7/1980 | Stenzenberger | |
| 4,211,861 A | 7/1980 | Stenzenberger | |
| 4,304,705 A | 12/1981 | Heilmann et al. | |
| 4,537,948 A | 8/1985 | Bartmann et al. | |
| 4,540,763 A | 9/1985 | Kirchhoff | |
| 4,562,243 A | 12/1985 | Percec | |
| 4,564,656 A * | 1/1986 | Cooper | C08F 285/00 525/152 |
| 4,642,126 A | 2/1987 | Zador et al. | |
| 4,642,329 A | 2/1987 | Kirchhoff et al. | |
| 4,652,274 A | 3/1987 | Boettcher et al. | |
| 4,661,193 A | 4/1987 | Kirchhoff et al. | |
| 4,665,137 A | 5/1987 | Percec | |
| 4,724,260 A | 2/1988 | Kirchhoff et al. | |
| 4,734,485 A | 3/1988 | Bartmann et al. | |
| 4,743,399 A | 5/1988 | Kirchhoff et al. | |
| 5,017,663 A | 5/1991 | Mizuno et al. | |
| 5,021,543 A | 6/1991 | Mayska et al. | |
| 5,202,409 A | 4/1993 | Tsukahara et al. | |
| 5,391,650 A | 2/1995 | Brennan et al. | |
| 5,521,244 A | 5/1996 | Yates et al. | |
| 5,543,516 A | 8/1996 | Ishida | |
| 6,307,010 B1 | 10/2001 | Braat et al. | |
| 6,384,176 B1 | 5/2002 | Braat et al. | |
| 6,576,800 B2 | 6/2003 | Higashimura et al. | |
| 6,627,704 B2 | 9/2003 | Yeager et al. | |
| 6,689,920 B2 | 2/2004 | Ishii et al. | |
| 6,794,481 B2 | 9/2004 | Amagai et al. | |
| 6,995,195 B2 | 2/2006 | Ishii et al. | |
| 7,071,266 B2 | 7/2006 | Ishli et al. | |
| 7,192,651 B2 | 3/2007 | Ohno et al. | |
| 7,193,019 B2 | 3/2007 | Norisue et al. | |
| 7,193,030 B2 | 3/2007 | Ohno et al. | |
| 7,393,904 B2 | 7/2008 | Ishii et al. | |
| 7,595,367 B2 | 9/2009 | Carrillo et al. | |
| 7,638,566 B2 | 12/2009 | Braidwood et al. | |

(Continued)

FOREIGN PATENT DOCUMENTS

| | | |
|---|---|---|
| CA | 2082735 A1 | 6/1993 |
| CN | 1914239 A | 2/2007 |

(Continued)

*Primary Examiner* — Shane Fang
(74) *Attorney, Agent, or Firm* — Cantor Colburn LLP

(57) ABSTRACT

A phenylene ether oligomer has repeating units of the structure

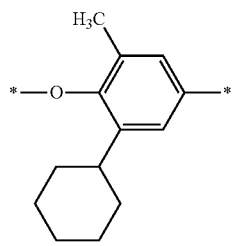

and less than 30 weight percent of repeating units derived from a monohydric phenol having identical substituents in the 2- and 6-positions, wherein the phenylene ether oligomer includes a vinyl benzene ether end group, an amine end group, maleimide end group, a norbornene end group, an anhydride end group, or a combination comprising at least one of the foregoing. The phenylene ether oligomer can be used to provide a curable composition. The curable composition can be cured to provide a thermoset composition. Articles comprising the thermoset composition are also described.

15 Claims, No Drawings

(56) References Cited

U.S. PATENT DOCUMENTS

| | | |
|---|---|---|
| 7,662,906 B2 | 2/2010 | Uera et al. |
| 7,671,167 B2 | 3/2010 | Carrillo et al. |
| 7,951,877 B2 | 5/2011 | Nakano et al. |
| 8,017,697 B2 | 12/2011 | Carrillo et al. |
| 8,669,332 B2 | 3/2014 | Carrillo et al. |
| 9,062,145 B2 | 6/2015 | Ohno et al. |
| 2002/0028907 A1 | 3/2002 | Higashimura et al. |
| 2003/0194562 A1 | 10/2003 | Ishii et al. |
| 2004/0147715 A1 | 5/2004 | Ishii et al. |
| 2004/0152848 A1 | 6/2004 | Ishii et al. |
| 2004/0198863 A1 | 10/2004 | Ishii et al. |
| 2005/0042466 A1 | 2/2005 | Ohno et al. |
| 2005/0090624 A1 | 4/2005 | Norisue et al. |
| 2006/0160982 A1 | 7/2006 | Ishii et al. |
| 2007/0106051 A1 | 5/2007 | Carrillo et al. |
| 2007/0232730 A1 | 10/2007 | Itagaki et al. |
| 2008/0076884 A1* | 3/2008 | Yeager .................. C08L 71/123 525/534 |
| 2008/0076885 A1 | 3/2008 | Yeager et al. |
| 2009/0012331 A1* | 1/2009 | Nakano .................. C08G 65/44 568/658 |
| 2009/0306399 A1 | 12/2009 | Nishino et al. |
| 2012/0329961 A1* | 12/2012 | Carrillo .................. C08G 77/46 525/92 A |
| 2013/0146344 A1 | 6/2013 | Lee et al. |
| 2015/0218326 A1 | 8/2015 | Kitai et al. |

FOREIGN PATENT DOCUMENTS

| | | |
|---|---|---|
| CN | 102002159 A | 4/2011 |
| CN | 105017520 B | 8/2017 |
| EP | 0549977 A1 | 7/1993 |
| JP | H06220226 A | 8/1994 |
| JP | 2006316092 A | 11/2006 |
| JP | 4145125 B2 | 9/2008 |
| JP | 4697415 B2 | 6/2011 |
| JP | 4824658 B2 | 11/2011 |
| JP | 5192198 B2 | 5/2013 |
| WO | 2002012370 | 2/2002 |
| WO | 2008036454 A1 | 3/2008 |
| WO | 2013162639 A1 | 10/2013 |
| WO | 2016141707 A1 | 9/2016 |

\* cited by examiner

PHENYLENE ETHER OLIGOMER, CURABLE COMPOSITION COMPRISING THE PHENYLENE ETHER OLIGOMER, AND THERMOSET COMPOSITION DERIVED THEREFROM

CROSS REFERENCE TO RELATED APPLICATIONS

This application claims the benefit of European Application No. 18170027.9, filed Apr. 30, 2018, which is incorporated by reference in its entirety herein.

BACKGROUND

Thermoset resins are materials that cure to form very hard plastics. These materials that can be used in a wide variety of consumer and industrial products. For example, thermosets are used in protective coatings, adhesives, electronic laminates (such as those used in the fabrication of computer circuit boards), flooring, and paving applications glass fiber-reinforced pipes, and automotive parts (including leaf springs, pumps, and electrical components). Relative to other types of plastics, cured thermosets are typically brittle. It would therefore be desirable to retain the good properties of thermosets and also reduce their brittleness.

Poly(arylene ether) resins, sometimes called polyphenylene ethers, have been disclosed as additives to reduce the brittleness (improve the toughness) of cured thermosets. For example, it is known to combine certain poly(arylene ether) resins with thermosets resins such as epoxies, cyanate esters, maleimides, acrylates, and benzoxazine resins. These poly(arylene ether)-containing compositions are often processed in solvents to reduce the viscosity of the curable composition and to enhance impregnation of the curable composition into fillers and/or reinforcements. When a solvent is used, it would be preferable to use a non-chlorinated hydrocarbon solvent. However, non-chlorinated hydrocarbon solvents such as N-methyl-2-pyrrolidone (NMP), toluene, and xylene are not ideal for this purpose because they produce phase-separated mixtures with poly(2,6-dimethyl-1,4-phenylene ether) at room temperature. Improvements in the miscibility of poly(arylene ether)s and solvents have been obtained by processing curable compositions containing them at elevated temperatures as described, for example, in Japanese Patent Application Publication No. JP 06-220226 A of Katayose et al. However, it would be desirable to avoid the use of elevated temperatures because they are associated with increased solvent flammability, increased solvent emissions, and increased energy costs. It can also be desirable to use concentrated solutions of poly(phenylene ether)s to maximize the amount of poly(phenylene ether) added to a curable composition while minimizing the amount of solvent.

There is therefore a need to develop materials and methods providing stable, homogeneous phenylene ether solutions in non-halogenated solvents such as NMP and MEK. Moreover, the solutions are preferably resistant to phase separation and precipitation, and can have low solution viscosity at and below room temperature. Such compositions can be used in curable compositions to ultimately provide improved thermoset compositions.

BRIEF DESCRIPTION

A phenylene ether oligomer comprises repeating units of the structure

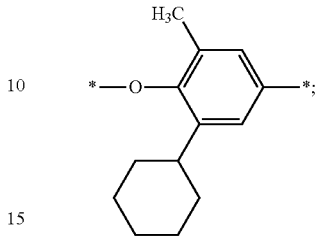

wherein the phenylene ether oligomer comprises less than 30 weight percent of repeating units derived from a monohydric phenol having identical substituents in the 2- and 6-positions; and wherein the phenylene ether oligomer comprises a vinyl benzene ether end group, an amine end group, maleimide end group, a norbornene end group, an anhydride group, or a combination comprising at least one of the foregoing.

A method of making the phenylene ether oligomer comprises oxidatively polymerizing 2-methyl-6-cyclohexyl phenol in the presence of a catalyst to provide the phenylene ether oligomer.

A curable composition comprises the phenylene ether oligomer; and a curing promoter.

A thermoset composition comprises a cured product of the curable composition, preferably wherein the thermoset composition has a glass transition temperature of greater than or equal to 180° C., preferably greater than or equal to 190° C., more preferably greater than or equal to 200° C.

An article comprises the thermoset composition, preferably wherein the article is in the form of a composite, a foam, a fiber, a layer, a coating, an encapsulant, an adhesive, a sealant, a molded component, a prepreg, a casing, a laminate, a metal clad laminate, an electronic composite, a structural composite, or a combination comprising at least one of the foregoing.

A method for the manufacture of a thermoset composition, the method comprising curing the curable composition, preferably at a temperature of 50 to 250° C.

The above described and other features are exemplified by the following detailed description.

DETAILED DESCRIPTION

The present inventors have determined that phenylene ether oligomers derived from 2-methyl-6-cyclohexylphenol have increased solubility in non-halogenated solvents and lower solution viscosity than phenylene ether oligomers in which the 2-methyl-6-cyclohexylphenol is partially or completely replaced by 2,6-dimethylphenol. With this improvement, stable solutions of phenylene ether oligomers in non-halogenated solvents having reduced viscosity can be prepared. Additionally, the phenylene ether oligomers of the present disclosure have a linear architecture. Advantageously, the phenylene ether oligomers can be used to prepare thermoset compositions for a variety of applications.

Accordingly, an aspect of the present disclosure is a phenylene ether oligomer comprising repeating units having the structure

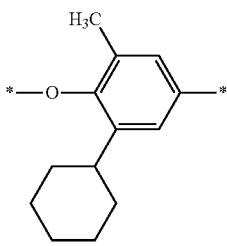

The oligomer can consist of the above repeating units derived from 2-methyl-6-cyclohexylphenol or can comprise repeating units derived from a monohydric phenol different from 2-methyl-6-cyclohexylphenol. When the oligomer comprises additional repeating units, the phenylene ether oligomer comprises less than 30 weight percent of repeating units derived from a monohydric phenol having identical substituents in the 2- and 6-positions (e.g., 2,6-dimethylphenol, 2,3,6-dimethylphenol, and the like, or combinations thereof).

The phenylene ether oligomer has a number average molecular weight (Mn) of 600 to 5,000 grams per mole, for example 600 to 3,500 grams per mole, or 1,000 to 5,000 grams per mole, or 1,000 to 3,500 grams per mole. Number average molecular weight can be determined by, for example, gel permeation chromatography relative to polystyrene standards.

The phenylene ether oligomer of the present disclosure can advantageously have a low intrinsic viscosity, for example, an intrinsic viscosity of less than 0.15 deciliter per gram, or 0.02 to 0.15 deciliter per gram, or 0.03 to 0.10 deciliter per gram, or 0.035 to 0.075 deciliter per gram. Intrinsic viscosity can be measured by Ubbelohde viscometer at 25° C. in chloroform.

The phenylene ether oligomer is a functionalized phenylene ether oligomer comprising at least one functional end group. The phenylene ether oligomer can be monofunctional (i.e., having a functional group at one terminus of the oligomer) or bifunctional. The functional group can be, for example, a vinyl benzene ether group, an amine group, a maleimide group, a norbornene group, an anhydride group, or a combination comprising at least one of the foregoing. In a specific embodiment, the functional group can be a vinyl benzene ether group.

In some embodiments, the functionalized phenylene ether oligomer is a bifunctional phenylene ether oligomer. For example, it can have functional groups at both termini of the oligomer chain (i.e., having an average functionality of 2). Bifunctional polymers with functional groups at both termini of the polymer chains are also referred to as "telechelic" polymers. In some embodiments, the phenylene ether oligomer comprises a bifunctional phenylene ether oligomer having the structure

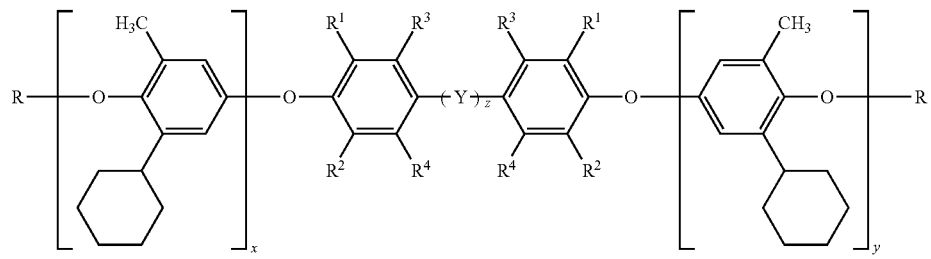

wherein $R^1$ and $R^2$ are each independently halogen, unsubstituted or substituted $C_1$-$C_{12}$ primary or secondary hydrocarbyl, $C_1$-$C_{12}$ hydrocarbylthio, $C_1$-$C_{12}$ hydrocarbyloxy, or $C_2$-$C_{12}$ halohydrocarbyloxy wherein at least two carbon atoms separate the halogen and oxygen atoms; each occurrence of $R^3$ and $R^4$ are each independently hydrogen, halogen, unsubstituted or substituted $C_1$-$C_{12}$ primary or secondary hydrocarbyl, $C_1$-$C_{12}$ hydrocarbylthio, $C_1$-$C_{12}$ hydrocarbyloxy, or $C_2$-$C_{12}$ halohydrocarbyloxy wherein at least two carbon atoms separate the halogen and oxygen atoms; x and y are independently 0 to 30, preferably 0 to 20, more preferably 0 to 15, still more preferably 0 to 10, even more preferably 0 to 8, provided that the sum of x and y is at least 2, preferably at least 3, more preferably at least 4; R is independently at each occurrence a vinyl benzene ether end group, an amine end group, or a maleimide end group a norbornene end group, an anhydride group; and Y has a structure comprising

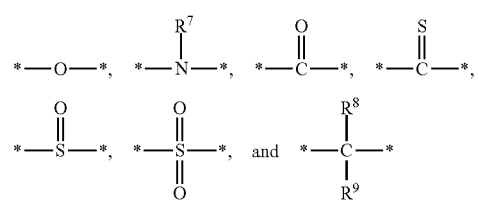

wherein each occurrence of $R^7$ is independently hydrogen or $C_1$-$C_{12}$ hydrocarbyl, and each occurrence of $R^8$ and $R^9$ is independently hydrogen, $C_1$-$C_{12}$ hydrocarbyl, or $C_1$-$C_6$ hydrocarbylene wherein $R^8$ and $R^9$ collectively form a $C_4$-$C_{12}$ alkylene group.

In a specific embodiment, in the above formula, each occurrence of $R^1$ and $R^2$ is methyl, each occurrence of $R^3$ and $R^4$ is hydrogen, Y is an isopropylidene group, and R is a vinyl benzyl group.

In some embodiments, the phenylene ether oligomer comprises a phenylene ether oligomer-polysiloxane block copolymer. As used herein, the term "phenylene ether oligomer-polysiloxane block copolymer" refers to a block copolymer comprising at least one phenylene ether oligomer block and at least one polysiloxane block.

In some embodiments, the phenylene ether oligomer-polysiloxane block copolymers can be the product of a process comprising oxidatively copolymerizing a monomer mixture comprising the 2-methyl-6-cyclohexylphenol and a hydroxyaryl-terminated polysiloxane. The hydroxyaryl-diterminated polysiloxane can comprise a plurality of repeating units having the structure

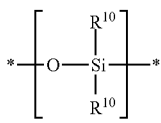

wherein each occurrence of $R^{10}$ is independently hydrogen, $C_1$-$C_{12}$ hydrocarbyl or $C_1$-$C_{12}$ halohydrocarbyl; and two terminal units having the structure

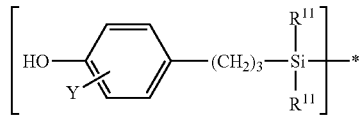

wherein Y is hydrogen, $C_1$-$C_{12}$ hydrocarbyl, $C_1$-$C_{12}$ hydrocarbyloxy, or halogen, and wherein each occurrence of $R^{11}$ is independently hydrogen, $C_1$-$C_{12}$ hydrocarbyl, or $C_1$-$C_{12}$ halohydrocarbyl. In a very specific embodiment, each occurrence of $R^{10}$ and $R^{11}$ is methyl, and Y is methoxy. Thus in some embodiments, the hydroxyaryl-terminated polysiloxane has the structure

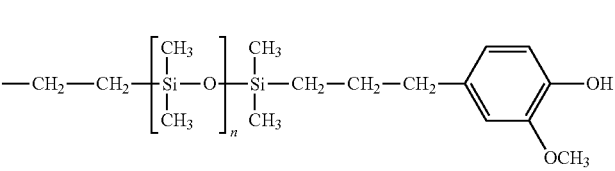

wherein n is, on average, 5 to 100, preferably 30 to 60.

In another specific embodiment, the phenylene ether oligomer-polysiloxane block copolymer can be a bifunctional phenylene ether oligomer-polysiloxane block copolymer having the structure

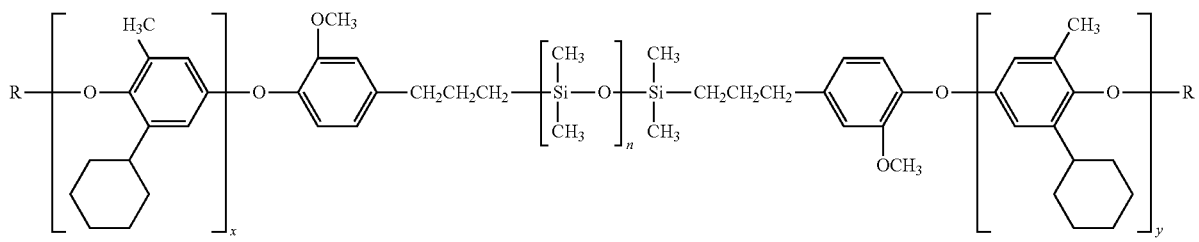

wherein n, x, y, and R can be as described above. In a very specific embodiment, R in the above formula can be a vinyl benzyl group.

The oxidative copolymerization method produces phenylene ether oligomer-polysiloxane block copolymer as the desired product phenylene ether oligomer (without an incorporated polysiloxane block) as a by-product. It is not necessary to separate the phenylene ether oligomer from the phenylene ether oligomer-polysiloxane block copolymer. The phenylene ether oligomer-polysiloxane block copolymer can thus be utilized as a "reaction product" that includes both the phenylene ether oligomer and the phenylene ether oligomer-polysiloxane block copolymer. Certain isolation procedures, such as precipitation from isopropanol, make it possible to assure that the reaction product is essentially free of residual hydroxyaryl-terminated polysiloxane starting material. In other words, these isolation procedures assure that the polysiloxane content of the reaction product is essentially all in the form of phenylene ether oligomer-polysiloxane block copolymer. Detailed methods for forming poly(phenylene ether)-polysiloxane block copolymers are described in U.S. Pat. Nos. 8,017,697 and 8,669,332 to Carrillo et al.

In some embodiments, the phenylene ether oligomer can include molecules having aminoalkyl-containing end-groups (also referred to herein as external amine content), typically located in a position ortho to the hydroxy group. As used herein, the term "external amine content" refers to the weight percent of amine-containing end-groups (e.g., (alkyl)$_2$N-containing end-groups, for example, 3-methyl-4-hydroxy-5-di-n-butylaminomethylphenyl groups) incorporated into the oligomer (also referred to as Mannich end-groups), based on the total weight of the phenylene ether oligomer composition. The amine-containing end-groups can be of the formula

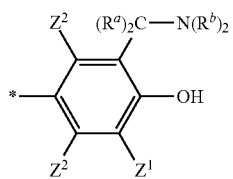

wherein $Z^1$ is halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy wherein at least two carbon atoms separate the halogen and oxygen atoms; and each occurrence of $Z^2$ is independently hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy wherein at least two carbon atoms separate the halogen and oxygen atoms. Each occurrence of $R^a$ is independently hydrogen or unsubstituted or substituted $C_1$-$C_{12}$ hydrocarbyl. Each occurrence of $R^b$ is independently an unsubstituted or substituted $C_1$-$C_{12}$ hydrocarbyl. In some embodiments, $Z^1$ is methyl, each occurrence of $Z^2$ is hydrogen, each occurrence of $R^a$ is hydrogen, and each occurrence of $R^b$ is n-butyl, and the amine-containing end-group is 3-methyl-4-hydroxy-5-di-n-butylaminomethylphenyl. The phenylene ether oligomer of the phenylene ether oligomer composition can have an external amine content of less than or equal to 1.5 weight percent, or greater than 0 to 1.5 weight percent, or 0.01 to 1.5 weight percent, or 0.01 to 1 weight percent, or 0.01 to 0.75 weight percent, or 0.01 to 0.5 weight percent, or 0.01 to 0.1 weight percent, or 0.025 to 1.5 weight percent, or 0.025 to 1 weight percent, or 0.025 to 0.75 weight percent, or 0.025 to 0.5 weight percent, or 0.025 to 0.1 weight percent, based on the total weight of the phenylene ether oligomer composition. In some embodiments, the phenylene ether oligomer can have an external amine content of less than or equal to 0.1 weight percent, or greater than 0 to 0.1 weight percent, or 0.01 to 0.08 weight percent, or 0.01 to 0.05 weight percent, or 0.025 to 0.08 weight percent, or 0.025 to 0.05 weight percent. In some embodiments, the phenylene ether oligomer can have an external amine content of 0.1 to 1.5 weight percent, or 0.1 to 1.4 weight percent, or 0.2 to 1.3 weight percent, or 0.5 to 1.25 weight percent. In some embodiments, the phenylene ether oligomer can be substantially free of external amine content, where "substantially free" means that no external amine content can be detected by proton nuclear magnetic resonance ($^1$H NMR) spectroscopy. In some embodiments, "substantially free" means that the phenylene ether oligomer does not comprise more than 0.025 weight percent, preferably not more than 0.01 weight percent external amine.

As mentioned above, the phenylene ether oligomer of the present disclosure comprises less than 30 weight percent of repeating units derived from a monohydric phenol having identical substituents in the 2- and 6-positions. Within this range, the oligomer can comprise less than 20, 10, 5, 1, or 0.1 weight percent of repeating units derived from a monohydric phenol having identical substituents in the 2- and 6-positions. The oligomer can comprise no repeating units derived from a monohydric phenol having identical substituents in the 2- and 6-positions. The monohydric phenol having identical substituents in the 2- and 6-positions of the phenolic ring can be 2,6-dimethylphenol. An example of a phenylene ether oligomer having no repeating units derived from monohydric phenols having identical substituents in the 2- and 6-positions of the phenolic ring has the structure

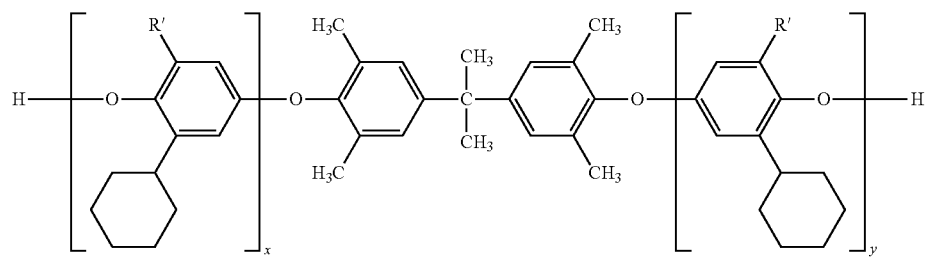

wherein R' is independently at each occurrence methyl or di(n-butyl)aminomethyl. It should be noted that in the structure above, the end group R is shown as hydrogen, however any of the end groups R described herein can be present on the above phenylene ether oligomer having no repeating units derived from monohydric phenols having identical substituents in the 2- and 6-positions of the phenolic ring. The oligomer comprises, on average, less than or equal to 0.005 weight percent of di(n-butyl)aminomethyl groups, based on the weight of the oligomer. The variables x and y can be as described above, and are, for example, independently integers from zero to 50, provided that the sum of x plus y is at least two. In some embodiments of this phenylene ether oligomer, the sum of x and y is 8 to 20.

In some embodiments, the phenylene ether oligomer of the present disclosure excludes repeating units derived from 2-cyclohexylphenol. As mentioned above, the phenylene ether oligomer of the present disclosure can be a linear phenylene ether oligomer.

The phenylene ether oligomer of the present disclosure can be made by oxidatively polymerizing 2-methyl-6-cyclohexyl phenol in the presence of a catalyst to provide the phenylene ether oligomer. In some embodiments, when the phenylene ether oligomer is a bifunctional phenylene ether oligomer, it can be formed by polymerization of monomers comprising 2-methyl-6-phenylphenol and dihydric phenol by continuous addition of oxygen to a reaction mixture comprising the monomers, solvent, and polymerization catalyst. The molecular oxygen ($O_2$) can be provided as air or pure oxygen. The polymerization catalyst is a metal complex comprising a transition metal cation. The metal cation can include ions from Group VIB, VIIB, VIIIB, or IB of the periodic table, or a combination thereof. Of these, chromium, manganese, cobalt, copper, and combinations comprising at least one of the foregoing ions can be used. In some embodiments, the metal ion is copper ion ($Cu^+$ and $Cu^{2+}$). Metal salts which can serve as sources of metal cations include cuprous chloride, cupric chloride, cuprous bromide, cupric bromide, cuprous iodide, cupric iodide, cuprous sulfate, cupric sulfate, cuprous tetraamine sulfate, cupric tetraamine sulfate, cuprous acetate, cupric acetate, cuprous propionate, cupric butyrate, cupric laurate, cuprous palmitate, cuprous benzoate, and the corresponding manganese salts and cobalt salts. Instead of use of any of the above-exemplified metal salts, it is also possible to add a metal or a metal oxide and an inorganic acid, organic acid or an aqueous solution of such an acid and form the corresponding metal salt or hydrate in situ. For example, cuprous oxide and hydrobromic acid can be added to generate cuprous bromide in situ.

The polymerization catalyst further comprises at least one amine ligand. The amine ligand can be, for example, a monoamine, an alkylene diamine, or a combination comprising at least one of the foregoing. Monoamines include dialkylmonoamines (such as di-n-butylamine, or DBA) and trialkylmonoamines (such as N,N-dimethylbutylamine, or DMBA). Diamines include alkylenediamines, such as N,N'-di-tert-butylethylenediamine, or DBEDA. Suitable dialkylmonoamines include dimethylamine, di-n-propylamine, di-n-butylamine, di-sec-butyl amine, di-tert-butylamine, dipentylamine, dihexylamine, dioctylamine, didecylamine, dibenzylamine, methylethylamine, methylbutylamine, dicyclohexylamine, N-phenylethanolamine, N-(p-methyl)phenylethanolamine, N-(2,6-dimethyl)phenylethanolamine, N-(p-chloro)phenylethanolamine, N-ethylaniline, N-butyl aniline, N-methyl-2-methylaniline, N-methyl-2,6-dimethylaniline, diphenylamine, and the like, or a combination thereof. Suitable trialkylmonoamines include trimethylamine, triethylamine, tripropylamine, tributylamine, butyldimethylamine, phenyldiethylamine, and the like, or a combination thereof.

Suitable alkylenediamines include those having the formula:

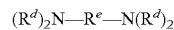

$(R^d)_2N-R^e-N(R^d)_2$ wherein $R^e$ is a substituted or unsubstituted divalent residue; and each $R^d$ is independently hydrogen or $C_1$-$C_8$ alkyl. In some examples, of the above formula, two or three aliphatic carbon atoms form the closest link between the two diamine nitrogen atoms. Specific alkylenediamine ligands include those in which $R^e$ is dimethylene ($-CH_2CH_2-$) or trimethylene ($-CH_2CH_2CH_2-$). $R^d$ can be independently hydrogen, methyl, propyl, isopropyl, butyl, or a $C_4$-$C_8$ alpha-tertiary alkyl group. Examples of alkylenediamine ligands include N,N,N',N' tetramethylethylene diamine (TMED), N,N'-di-tert-butylethylenediamine (DBEDA), N,N,N',N'-tetramethyl-1,3-diaminopropane (TMPD), N-methyl-1,3-diaminopropane, N,N'-dimethyl-1,3-diaminopropane, N,N,N'-dimethyl-1,3-diaminopropane, N-ethyl-1,3-diaminopropane, N-methyl-1,4-diaminobutane, N,N'-trimethyl-1,4-diaminobutane, N,N,N'-trimethyl-1,4-diaminobutane, N,N,N',N'-tetramethyl-1,4-diaminobutane, N,N,N',N'-tetramethyl-1,5-diaminopentane, or a combination thereof. In some embodiments, the amine ligand is di-n-butylamine (DBA), N,N-dimethylbutylamine (DMBA), N,N'-di-tert-butylethylenediamine (DBEDA), or combinations thereof. The catalyst can be prepared in situ by mixing a metal ion source (e.g., cuprous oxide and hydrobromic acid) and amine ligands. In some embodiments, the polymerization catalyst comprises copper ion, bromide ion, and N,N'-di-tert-butylethylenediamine.

The method of making the functionalized phenylene ether oligomer further comprises reacting the phenylene ether oligomer (e.g., the hydroxyl-terminated phenylene ether oligomer) with a compound comprising a vinyl benzene ether group, an amine group, maleimide group, a norbornene group, an anhydride group, or a combination comprising at least one of the foregoing to provide the functionalized phenylene ether oligomer. For example, when a functional phenylene ether having at least one vinyl benzyl ether end group is desired, the method can comprise reacting the hydroxyl-terminated phenylene ether oligomer with a vinyl benzyl halide (e.g., vinyl benzyl chloride). An exemplary synthesis is further described in the working examples below. Suitable compounds comprising the desired functional groups and a group reactive toward the hydroxyl-terminated phenylene ether oligomer can be readily determined by one skilled in the art.

The phenylene ether oligomer of the present disclosure, having at least one reactive functional group, is well suited for use as a reactive component in curable compositions. Thus a curable composition represents another aspect of the present disclosure. The curable composition comprises the phenylene ether oligomer and a curing promoter.

In some embodiments, the curable composition can further include an auxiliary curable resin, a curable unsaturated monomer composition, or both. The auxiliary curable resin can be a thermoset resin, for example, an epoxy resin, a cyanate ester resin, a maleimide resin, a benzoxazine resin, a vinylbenzyl ether resin, an arylcyclobutene resin, a perfluorovinyl ether resin, oligomers or polymers with curable vinyl functionality, or a combination thereof.

Epoxy resins useful as thermoset resins can be produced by reaction of phenols or polyphenols with epichlorohydrin to form polyglycidyl ethers. Examples of useful phenols for production of epoxy resins include substituted bisphenol A, bisphenol F, hydroquinone, resorcinol, tris-(4-hydroxyphenyl)methane, and novolac resins derived from phenol or o-cresol. Epoxy resins can also be produced by reaction of aromatic amines, such as p-aminophenol or methylenedianiline, with epichlorohydrin to form polyglycidyl amines. Epoxy resins can be converted into solid, infusible, and insoluble three dimensional networks by curing with cross-linkers, often called curing agents, or hardeners. Curing agents are either catalytic or coreactive. Coreactive curing agents have active hydrogen atoms that can react with epoxy groups of the epoxy resin to form a cross-linked resin. The active hydrogen atoms can be present in functional groups comprising primary or secondary amines, phenols, thiols, carboxylic acids, or carboxylic acid anhydrides. Examples of coreactive curing agents for epoxy resins include aliphatic and cycloaliphatic amines and amine-functional adducts with epoxy resins, Mannich bases, aromatic amines, polyamides, amidoamines, phenalkamines, dicyandiamide, polycarboxylic acid-functional polyesters, carboxylic acid anhydrides, amine-formaldehyde resins, phenol-formaldehyde resins, polysulfides, polymercaptans, or a combination comprising at least one of the foregoing coreactive curing agents. A catalytic curing agent functions as an initiator for epoxy resin homopolymerization or as an accelerator for coreactive curing agents. Examples of catalytic curing agents include tertiary amines, such as 2-ethyl-4-methylimidazole, Lewis acids, such as boron trifluoride, and latent cationic cure catalysts, such as diaryliodonium salts.

The thermoset resin can be a cyanate ester. Cyanate esters are compounds having a cyanate group (—O—C≡N) bonded to carbon via the oxygen atom, i.e. compounds with C—O—C≡N groups. Cyanate esters useful as thermoset resins can be produced by reaction of a cyanogen halide with a phenol or substituted phenol. Examples of useful phenols include bisphenols utilized in the production of epoxy resins, such as bisphenol A, bisphenol F, and novolac resins based on phenol or o-cresol. Cyanate ester prepolymers are prepared by polymerization/cyclotrimerization of cyanate esters. Prepolymers prepared from cyanate esters and diamines can also be used.

The thermoset resin can be a bismaleimide. Bismaleimide resins can be produced by reaction of a monomeric bismaleimide with a nucleophile such as a diamine, aminophenol, or amino benzhydrazide, or by reaction of a bismaleimide with diallyl bisphenol A. Specific examples of bismaleimide resins can include 1,2-bismaleimidoethane, 1,6-bismaleimidohexane, 1,3-bismaleimidobenzene, 1,4-bismaleimidobenzene, 2,4-bismaleimidotoluene, 4,4'-bismaleimidodiphenylmethane, 4,4'-bismaleimidodiphenylether, 3,3'-bismaleimidodiphenylsulfone, 4,4'-bismaleimidodiphenylsulfone, 4,4'-bismaleimidodicyclohexylmethane, 3,5-bis(4-maleimidophenyl)pyridine, 2,6-bismaleimidopyridine, 1,3-bis(maleimidomethyl)cyclohexane, 1,3-bis(maleimidomethyl)benzene, 1,1-bis(4-maleimidophenyl)cyclohexane, 1,3-bis(dichloromaleimido)benzene, 4,4'-bis(citraconimido)diphenylmethane, 2,2-bis(4-maleimidophenyl)propane, 1-phenyl-1,1-bis(4-maleimidophenyl)ethane, N,N-bis(4-maleimidophenyl)toluene, 3,5-bismaleimido-1,2,4-triazole N,N'-ethylenebismaleimide, N,N'-hexamethylenebismaleimide, N,N'-m-phenylenebismaleimide, N,N'-p-phenylenebismaleimide, N,N'-4,4'-diphenylmethanebismaleimide, N,N'-4,4'-diphenyletherbismaleimide, N,N'-4,4'-diphenylsufonebismaleimide, N,N'-4,4'-dicyclohexylmethanebismaleimide, N,N'-alpha,alpha'-4,4'-dimethylenecyclohexanebismaleimide, N,N'-m-methaxylenebismaleimide, N,N'-4,4'-diphenylcyclohexanebismaleimide, and N,N'-methylenebis(3-chloro-p-phenylene)bismaleimide, as well as the maleimide resins disclosed in U.S. Pat. No. 3,562,223 to Bargain et al., and U.S. Pat. Nos. 4,211,860 and 4,211,861 to Stenzenberger. Bismaleimide resins can be prepared by methods known in the art, as described, for example, in U.S. Pat. No. 3,018,290 to Sauers et al. In some embodiments, the bismaleimide resin is N,N'-4,4'-diphenylmethane bismaleimide.

The thermoset resin can be a benzoxazine resin. As is well known, benzoxazine monomers are made from the reaction of three reactants, aldehydes, phenols, and primary amines with or without solvent. U.S. Pat. No. 5,543,516 to Ishida describes a solventless method of forming benzoxazine monomers. An article by Ning and Ishida in Journal of Polymer Science, Chemistry Edition, vol. 32, page 1121 (1994) describes a procedure using a solvent. The procedure using solvent is generally common to the literature of benzoxazine monomers.

The preferred phenolic compounds for forming benzoxazines include phenols and polyphenols. The use of polyphenols with two or more hydroxyl groups reactive in forming benzoxazines may result in branched and/or cross-linked products. The groups connecting the phenolic groups into a phenol can be branch points or connecting groups in the polybenzoxazine.

Suitable phenols for use in the preparation of benzoxazine monomers include phenol, cresol, resorcinol, catechol, hydroquinone, 2-allylphenol, 3-allylphenol, 4-allylphenol, 2,6-dihydroxynaphthalene, 2,7-dihydrooxynapthalene, 2-(diphenylphosphoryl)hydroquinone, 2,2'-biphenol, 4,4-biphenol, 4,4'-isopropylidenediphenol (bisphenol A), 4,4'-isopropylidenebis(2-methylphenol), 4,4'-isopropylidenebis(2-allylphenol), 4,4'(1,3-phenylenediisopropylidene) bisphenol (bisphenol M), 4,4'-isopropylidenebis(3-phenylphenol) 4,4'-(1,4-phenylenediisoproylidene) bisphenol (bisphenol P), 4,4'-ethylidenediphenol (bisphenol E), 4,4'oxydiphenol, 4,4'thiodiphenol, 4,4'-sufonyldiphenol, 4,4'-sulfinyldiphenol, 4,4'-hexafluoroisoproylidene)bisphenol (Bisphenol AF), 4,4'(1-phenylethylidene)bisphenol (Bisphenol AP), bis(4-hydroxyphenyl)-2,2-dichloroethylene (Bisphenol C), Bis(4-hydroxyphenyl)methane (Bisphenol-F), 4,4'-(cyclopentylidene)diphenol, 4,4'-(cyclohexylidene) diphenol (Bisphenol Z), 4,4'-(cyclododecylidene)diphenol 4,4'-(bicyclo[2.2.1]heptylidene)diphenol, 4,4'-(9H-fluorene-9,9-diyl)diphenol, isopropylidenebis(2-allylphenol), 3,3-bis (4-hydroxyphenyl)isobenzofuran-1 (3H)-one, 1-(4-hydroxyphenyl)-3,3-dimethyl-2,3-dihydro-1H-inden-5-ol, 3,3, 3',3'-tetramethyl-2,2',3,3'-tetrahydro-1,1'-spirobi[indene]-5, 6'-diol (Spirobiindane), dihydroxybenzophenone (bisphenol K), tris(4-hydroxyphenyl)methane, tris(4-hydroxyphenyl) ethane, tris(4-hydroxyphenyl)propane, tris(4-hydroxyphenyl)butane, tris(3-methyl-4-hydroxyphenyl)methane, tetrakis(4-hydroxyphenyl)ethane dicyclopentadienylbis(2,6-dimethyl phenol), dicyclopentadienyl bis(ortho-cresol), dicyclopentadienyl bisphenol, and the like.

The aldehydes used to form the benzoxazine can be any aldehyde. In some embodiments, the aldehyde has 1 to 10 carbon atoms. In some embodiments, the aldehyde is formaldehyde. The amine used to form the benzoxazine can be an aromatic amine, an aliphatic amine, an alkyl substituted aromatic, or an aromatic substituted alkyl amine. The amine can also be a polyamine, although the use of polyamines will, under some circumstances, yield polyfunctional benzoxazine monomers. Polyfunctional benzoxazine monomers are more likely to result in branched and/or crosslinked polybenzoxazines than monofunctional benzoxazines, which would be anticipated to yield thermoplastic polybenzoxazines.

The amines for forming benzoxazines generally have 1 to 40 carbon atoms unless they include aromatic rings, and then they may have 6 to 40 carbon atoms. The amine of di- or polyfunctional may also serve as a branch point to connect one polybenzoxazine to another.

Thermal polymerization has been the preferred method for polymerizing benzoxazine monomers. The temperature to induce thermal polymerization is typically varied from 150 to 300° C. The polymerization is typically done in bulk, but could be done from solution or otherwise. Catalysts, such as carboxylic acids, have been known to slightly lower the polymerization temperature or accelerate the polymerization rate at the same temperature.

The thermoset resin can be a vinylbenzyl ether resin. Vinyl benzyl ether resins can be most readily prepared from condensation of a phenol with a vinyl benzyl halide, such as vinylbenzyl chloride to produce a vinylbenzyl ether. Bisphenol-A and trisphenols and polyphenols are generally used to produce poly(vinylbenzyl ethers) which may be used to produce crosslinked thermosetting resins. Vinyl benzyl ethers useful in the present composition can include those vinylbenzyl ethers produced from reaction of vinylbenzyl chloride or vinylbenzyl bromide with resorcinol, catechol, hydroquinone, 2,6-dihydroxy naphthalene, 2,7-dihydroxynapthalene, 2-(diphenylphosphoryl)hydroquinone, bis (2,6-dimethylphenol) 2,2'-biphenol, 4,4-biphenol, 2,2',6,6'-tetramethylbiphenol, 2,2',3,3',6,6'-hexamethylbiphenol, 3,3', 5,5'-tetrabromo-2,2'6,6'-tetramethylbiphenol, 3,3'-dibromo-2,2',6,6'-tetramethylbiphenol, 2,2',6,6'-tetramethyl-3,3'5-dibromobiphenol, 4,4'-isopropylidenediphenol (bisphenol A), 4,4'-isopropylidenebis(2,6-dibromophenol) (tetrabromo-bisphenol A), 4,4'-isopropylidenebis(2,6-dimethylphenol) (teramethylbisphenol A), 4,4'-isopropylidenebis(2-methylphenol), 4,4'-isopropylidenebis(2-allylphenol), 4,4'(1,3-phenylenediisopropylidene)bisphenol (bisphenol M), 4,4'-isopropylidenebis(3-phenylphenol) 4,4'-(1,4-phenylenediisoproylidene)bisphenol (bisphenol P), 4,4'-ethylidenediphenol (bisphenol E), 4,4'-oxydiphenol, 4,4'-thiodiphenol, 4,4'-thiobis(2,6-dimethylphenol), 4,4'-sufonyldiphenol, 4,4'-sulfonylbis(2,6-dimethylphenol) 4,4'-sulfinyldiphenol, 4,4'-hexafluoroisoproylidene)bisphenol (Bisphenol AF), 4,4'(1-phenylethylidene)bisphenol (Bisphenol AP), bis(4-hydroxyphenyl)-2,2-dichloroethylene (Bisphenol C), bis(4-hydroxyphenyl)methane (Bisphenol-F), bis (2,6-dimethyl-4-hydroxyphenyl)methane, 4,4'-(cyclopentylidene)diphenol, 4,4'-(cyclohexylidene)diphenol (Bisphenol Z), 4,4'-(cyclododecylidene)diphenol 4,4'-(bicyclo[2.2.1]heptylidene)diphenol, 4,4'-(9H-fluorene-9,9-diyl) diphenol, 3,3-bis(4-hydroxyphenyl)isobenzofuran-1(3H)-one, 1-(4-hydroxyphenyl)-3,3-dimethyl-2,3-dihydro-1H-inden-5-ol, 1-(4-hydroxy-3,5-dimethylphenyl)-1,3,3,4,6-pentamethyl-2,3-dihydro-1H-inden-5-ol, 3,3,3',3'-tetramethyl-2,2',3,3'-tetrahydro-1,1'-spirobi[indene]-5,6'-diol (Spirobiindane), dihydroxybenzophenone (bisphenol K), tris(4-hydroxyphenyl)methane, tris(4-hydroxyphenyl)ethane, tris(4-hydroxyphenyl)propane, tris(4-hydroxyphenyl)butane, tris(3-methyl-4-hydroxyphenyl)methane, tris(3, 5-dimethyl-4-hydroxyphenyl)methane, tetrakis(4-hydroxyphenyl)ethane, tetrakis(3,5-dimethyl-4-hydroxyphenyl)ethane, bis(4-hydroxyphenyl) phenylphosphine oxide, dicyclopentadienylbis(2,6-dimethyl phenol), dicyclopentadienyl bis(ortho-cresol), dicyclopentadienyl bisphenol, and the like.

The thermoset resin can be an arylcyclobutene resin. Arylcyclobutenes include those derived from compounds of the general structure

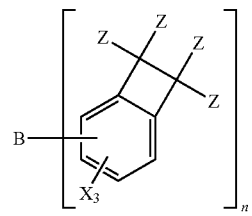

wherein B is an organic or inorganic radical of valence n (including carbonyl, sulfonyl, sulfinyl, sulfide, oxy, alkylphosphonyl, arylphosphonyl, isoalkylidene, cycloalkylidene, arylalkylidene, diarylmethylidene, methylidene dialkylsilanyl, arylalkylsilanyl, diarylsilanyl and $C_6$-$C_{20}$ phenolic compounds); each occurrence of X is independently hydroxy or $C_1$-$C_{24}$ hydrocarbyl (including linear and branched alkyl and cycloalkyl); and each occurrence of Z is independently hydrogen, halogen, or $C_1$-$C_{12}$ hydrocarbyl; and n is 1 to 1000, preferably 1 to 8, more preferably 2, 3, or 4. Other useful arylcyclobutenes and methods of arylcyclobutene synthesis can be found in U.S. Pat. Nos. 4,743, 399, 4,540,763, 4,642,329, 4,661,193, and 4,724,260 to Kirchhoff et al., and U.S. Pat. No. 5,391,650 to Brennan et al.

The thermoset resin can be a perfluorovinyl ether resin. Perfluorovinyl ethers are typically synthesized from phenols and bromotetrafluoroethane followed by zinc catalyzed reductive elimination producing ZnFBr and the desired perfluorovinylether. By this route bis, tris, and other polyphenols can produce bis-, tris- and poly(perfluorovinylether) s. Phenols useful in their synthesis include resorcinol, catechol, hydroquinone, 2,6-dihydroxy naphthalene, 2,7-dihydroxynapthalene, 2-(diphenylphosphoryl) hydroquinone, bis(2,6-dimethylphenol) 2,2'-biphenol, 4,4-biphenol, 2,2',6,6'-tetramethylbiphenol, 2,2',3,3',6,6'-hexamethylbiphenol, 3,3',5,5'-tetrabromo-2,2'6,6'-tetramethylbiphenol, 3,3'-dibromo-2,2',6,6'-tetramethylbiphenol, 2,2',6,6'-tetramethyl-3,3'5-dibromobiphenol, 4,4'-isopropylidenediphenol (bisphenol A), 4,4'-isopropylidenebis(2,6-dibromophenol) (tetrabromo-bisphenol A), 4,4'-isopropylidenebis(2,6-dimethylphenol) (teramethylbisphenol A), 4,4'-isopropylidenebis(2-methylphenol), 4,4'-isopropylidenebis(2-allylphenol), 4,4'(1,3-phenylenediisopropylidene)bisphenol (bisphenol M), 4,4'-isopropylidenebis(3-phenylphenol) 4,4'-(1,4-phenylenediisoproylidene)bisphenol (bisphenol P), 4,4'-ethylidenediphenol (bisphenol E), 4,4'oxydiphenol, 4,4'thiodiphenol, 4,4'thiobis(2,6-dimethylphenol), 4,4'-sufonyldiphenol, 4,4'-sulfonylbis(2,6-dimethylphenol) 4,4'-sulfinyldiphenol, 4,4'-hexafluoroisoproylidene)bisphenol (Bisphenol AF), 4,4'(1-phenylethylidene)bisphenol (Bisphenol AP), bis(4-hydroxyphenyl)-2,2-dichloroethylene (Bisphenol C), bis(4-hydroxyphenyl)methane (Bisphenol-F), bis (2,6-dimethyl-4-hydroxyphenyl)methane, 4,4'-(cyclopentylidene)diphenol, 4,4'-(cyclohexylidene)diphenol (Bisphenol Z), 4,4'-(cyclododecylidene)diphenol 4,4'-(bicyclo[2.2.1]heptylidene)diphenol, 4,4'-(9H-fluorene-9,9-diyl) diphenol, 3,3-bis(4-hydroxyphenyl)isobenzofuran-1(3H)-one, 1-(4-hydroxyphenyl)-3,3-dimethyl-2,3-dihydro-1H-inden-5-ol, 1-(4-hydroxy-3,5-dimethylphenyl)-1,3,3,4,6-pentamethyl-2,3-dihydro-1H-inden-5-ol, 3,3,3',3'- tetramethyl-2,2',3,3'-tetrahydro-1,1'-spirobi[indene]-5,6'-diol (Spirobiindane), dihydroxybenzophenone (bisphenol K), tris(4-hydroxyphenyl)methane, tris(4-hydroxyphenyl) ethane, tris(4-hydroxyphenyl)propane, tris(4-hydroxyphenyl)butane, tris(3-methyl-4-hydroxyphenyl)methane, tris(3,5-dimethyl-4-hydroxyphenyl)methane, tetrakis(4-hydroxyphenyl)ethane, tetrakis(3,5-dimethyl-4-hydroxyphenyl)ethane, bis(4-hydroxyphenyl) phenylphosphine oxide, dicyclopentadienylbis(2,6-dimethyl phenol), dicyclopentadienyl bis(2-methylphenol), dicyclopentadienyl bisphenol, and the like.

The thermoset resin can be an oligomer or polymer with curable vinyl functionality. Such materials include oligomers and polymers having crosslinkable unsaturation. Examples include styrene butadiene rubber (SBR), butadiene rubber (BR), and nitrile butadiene rubber (NBR) having unsaturated bonding based on butadiene; natural rubber (NR), isoprene rubber (IR), chloroprene rubber (CR), butyl rubber (IIR), and halogenated butyl rubber having unsaturated bonding based on isoprene; ethylene-α-olefin copolymer elastomers having unsaturated bonding based on dicyclopentadiene (DCPD), ethylidene norbornene (ENB), or 1,4-dihexadiene (1,4-HD) (namely, ethylene-α-olefin copolymers obtained by copolymerizing ethylene, an α-olefin, and a diene, such as ethylene-propylene-diene terpolymer (EPDM) and ethylene-butene-diene terpolymer (EBDM). In some embodiments, an EBDM is used.

Examples also include hydrogenated nitrile rubber, fluorocarbon rubbers such as vinylidenefluoride-hexafluoropropene copolymer and vinylidenefluoride-pentafluoropropene copolymer, epichlorohydrin homopolymer (CO), copolymer rubber (ECO) prepared from epichlorohydrin and ethylene oxide, epichlorohydrin allyl glycidyl copolymer, propylene oxide allyl glycidyl ether copolymer, propylene oxide epichlorohydrin allyl glycidyl ether terpolymer, acrylic rubber (ACM), urethane rubber (U), silicone rubber (Q), chlorosulfonated polyethylene rubber (CSM), polysulfide rubber (T) and ethylene acrylic rubber. Further examples include various liquid rubbers, for example various types of liquid butadiene rubbers, and the liquid atactic butadiene rubber that is butadiene polymer with 1,2-vinyl connection prepared by anionic living polymerization. It is also possible to use liquid styrene butadiene rubber, liquid nitrile butadiene rubber (CTBN, VTBN, ATBN, etc. by Ube Industries, Ltd.), liquid chloroprene rubber, liquid polyisoprene, dicyclopentadiene type hydrocarbon polymer, and polynorbornene (for example, as sold by Elf Atochem).

Polybutadiene resins, generally polybutadienes containing high levels of 1,2 addition are desirable for thermosetting matrices. Examples include the functionalized polybutadienes and poly(butadiene-styrene) random copolymers sold by Ricon Resins, Inc. under the trade names RICON, RICACRYL, and RICOBOND resins. These include butadienes containing both low vinyl content such as RICON 130, 131, 134, 142; polybutadienes containing high vinyl content such as RICON 150, 152, 153, 154, 156, 157, and P30D; random copolymers of styrene and butadiene including RICON 100, 181, 184, and maleic anhydride grafted polybutadienes and the alcohol condensates derived therefrom such as RICON 130MA8, RICON MA13, RICON 130MA20, RICON 131MAS, RICON 131MA10, RICON MA17, RICON MA20, RICON 184MA6 and RICON 156MA17. Also included are polybutadienes that can be used to improve adhesion including RICOBOND 1031, RICOBOND 1731, RICOBOND 2031, RICACRYL 3500, RICOBOND 1756, RICACRYL 3500; the polybutadienes RICON 104 (25% polybutadiene in heptane), RICON 257 (35% polybutadiene in styrene), and RICON 257 (35% polybutadiene in styrene); (meth)acrylic functionalized polybutadienes such as polybutadiene diacrylates and polybutadiene dimethacrylates. These materials are sold under the tradenames RICACRYL 3100, RICACRYL 3500, and RICACRYL 3801. Also are included are powder dispersions of functional polybutadiene derivatives including, for example, RICON 150D, 152D, 153D, 154D, P30D, RICOBOND 0 1731 HS, and RICOBOND 1756HS. Further butadiene resins include poly(butadiene-isoprene) block and random copolymers, such as those with molecular weights from 3,000-50,000 grams per mole and polybutadiene homopolymers having molecular weights from 3,000-50,000 grams per mole. Also included are polybutadiene, polyisoprene, and polybutadiene-isoprene copolymers functionalized with maleic anhydride functions, 2-hydroxyethylmaleic functions, or hydroxylated functionality.

Further examples of oligomers and polymers with curable vinyl functionality include unsaturated polyester resins based on maleic anhydride, fumaric acid, itaconic acid and citraconic acid; unsaturated epoxy (meth)acrylate resins containing acryloyl groups, or methacryloyl group; unsaturated epoxy resins containing vinyl or allyl groups, urethane (meth)acrylate resin, polyether (meth)acrylate resin, polyalcohol (meth)acrylate resins, alkyd acrylate resin, polyester acrylate resin, spiroacetal acrylate resin, diallyl phthalate resin, diallyl tetrabromophthalate resin, diethyleneglycol bisallylcarbonate resin, and polyethylene polythiol resins.

Crosslinking agents may be added, such as compounds containing alkene or alkyne functionality. These include, for example, such maleimides as N,N'-m-phenylene bismaleimide, triallylisocyanurate, trimethallylisocyanurate, trimethallylcyanurate, and triallylcyanurate.

Combinations of any one or more of the foregoing thermoset resins can be used as the auxiliary resin when present in the curable composition.

In some embodiments, the curable composition comprises the curable unsaturated monomer composition. The curable unsaturated monomer composition can include, for example, a monofunctional styrenic compound (e.g., styrene), a monofunctional (meth)acrylic compound, a polyfunctional allylic compound, a polyfunctional (meth)acrylate, a polyfunctional (meth)acrylamide, a polyfunctional styrenic compound, or a combination thereof. For example, in some embodiments, the curable unsaturated monomer composition can be an alkene-containing monomer or an alkyne-containing monomer. Suitable alkene- and alkyne-containing monomers include those described in U.S. Pat. No. 6,627,704 to Yeager et al. Suitable alkene-containing monomers include acrylate, methacrylate, and vinyl ester functionalized materials capable of undergoing free radical polymerization. Of particular use are acrylate and methacrylate materials. They can be monomers and/or oligomers such as (meth)acrylates, (meth)acrylamides, N-vinylpyrrolidone and vinylazlactones as disclosed in U.S. Pat. No. 4,304,705 of Heilman et al. Such monomers include mono-, di-, and polyacrylates and methacrylates, such as methyl acrylate, methyl methacrylate, ethyl acrylate, isopropyl methacrylate, isooctyl acrylate, isobornyl acrylate, isobornyl methacrylate, acrylic acid, n-hexyl acrylate, tetrahydrofurfuryl acrylate, N-vinylcaprolactam, N-vinylpyrrolidone, acrylonitrile, stearyl acrylate, allyl acrylate, glycerol diacrylate, glycerol triacrylate, ethylene glycol diacrylate, diethylene glycol diacrylate, triethylene glycol dimethacrylate, 1,6-hexanediol diacrylate, 1,3-propanediol diacrylate, 1,3-propanediol dimethacrylate, trimethylolpropane triacrylate, 1,2,4-butanetriol trimethacrylate, 2-phenoxyethyl acrylate, 1,4-cyclohexanediol diacrylate, pentaerythritol triacrylate, pentaerythritol tetraacrylate, pentaerythritol tetramethacrylate, sorbitol hexaacrylate, bis[1-(2-acryloxy)]-p-ethoxyphenyldimethylmethane, 2,2-bis[1-(3-acryloxy-2-hydroxy)]propoxyphenylpropane, tris(hydroxyethyl)isocyanurate trimethacrylate; the bis-acrylates and bis-methacrylates of polyethylene glycols of molecular weight average 200-500 grams per mole, bis-acrylates and bis-methacrylates of polybutadienes of molecular weight average 1000-10,000 grams per mole, copolymerizable mixtures of acrylated monomers such as those disclosed in U.S. Pat. No. 4,652,274 to Boettcher et al. and acrylated oligomers such as those disclosed in U.S. Pat. No. 4,642,126 to Zador et al.

It may be desirable to crosslink the alkene- or alkyne-containing monomer. Particularly useful as crosslinker compounds are acrylates such as allyl acrylate, glycerol diacrylate, glycerol triacrylate, ethylene glycol diacrylate, diethylene glycol diacrylate, triethylene glycol dimethacrylate, 1,6-hexanediol diacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexaacrylate, bis[1-(2-acryloxy)]-p-ethoxyphenyldi-methylmethane, 2,2-bis[1-(3-acryloxy-2-hydroxy)]propoxyphenylpropane, tris(hydroxyethyl)isocyanurate trimethacrylate; and the bis-acrylates and bis-methacrylates of polyethylene glycols of average molecular weight 200-500 grams per mole.

Also included are allylic resins and styrenic resins for example triallylisocyanurate and trimethallylisocyanurate, trimethallylcyanurate triallylcyanurate, divinyl benzene, dibromostyrene, and others described in U.S. Pat. No. 6,627,704 to Yeager et al.

A suitable curing promoter can be selected based on the functional group present on the phenylene ether oligomer and, when present, the auxiliary curable resin or the curable unsaturated monomer composition. For example, the curing promoter can comprise an amine, a dicyandiamide, a polyamide, an amidoamine, a Mannich base, an anhydride, a phenol-formaldehyde resin, a carboxylic acid functional polyester, a polysulfide, a polymercaptan, an isocyanate, a cyanate ester, or a combination thereof.

In addition to the phenylene ether oligomer, the curing promoter, and, when present, the auxiliary resin or unsaturated monomer composition, the curable composition can, optionally, comprise a solvent. The solvent can have an atmospheric boiling point of 50 to 250° C. A boiling point in this range facilitates removal of solvent from the curable composition while minimizing or eliminating the effects of bubbling during solvent removal.

The solvent can be, for example, a $C_3$-$C_8$ ketone, a $C_3$-$C_8$ N,N-dialkylamide, a $C_4$-$C_{16}$ dialkyl ether, a $C_6$-$C_{12}$ aromatic hydrocarbon, a $C_1$-$C_3$ chlorinated hydrocarbon, a $C_3$-$C_6$ alkyl alkanoate, a $C_2$-$C_6$ alkyl cyanide, or a combination thereof. The carbon number ranges refer to the total number of carbon atoms in the solvent molecule. For example, a $C_4$-$C_{16}$ dialkyl ether has 4 to 16 total carbon atoms, and the two alkyl groups can be the same or different. As other examples, the 3 to 8 carbon atoms in the "N,N-dialkylamide" include the carbon atom in the amide group, and the 2 to 6 carbons in the "$C_2$-$C_6$ alkyl cyanides" include the carbon atom in the cyanide group. Specific ketone solvents include, for example, acetone, methyl ethyl ketone, methyl isobutyl ketone, or a combination thereof. Specific $C_4$-$C_8$ N,N-dialkylamide solvents include, for example, dimethylformamide, dimethylacetamide, N-methyl-2-pyrrolidone (Chemical Abstracts Service Registry No. 872-50-4), or a combination thereof. Specific dialkyl ether solvents include, for example, tetrahydrofuran, ethylene glycol monomethylether, dioxane, or a combination thereof. In some embodiments, the $C_4$-$C_{16}$ dialkyl ethers include cyclic ethers such as tetrahydrofuran and dioxane. In some embodiments, the $C_4$-$C_{16}$ dialkyl ethers are noncyclic. The dialkyl ether can, optionally, further include one or more ether oxygen atoms within the alkyl groups and one or more hydroxy group substituents on the alkyl groups. The aromatic hydrocarbon solvent can comprise an ethylenically unsaturated solvent. Specific aromatic hydrocarbon solvents include, for example, benzene, toluene, xylenes, styrene, divinyl benzenes, or a combination thereof. The aromatic hydrocarbon solvent is preferably non-halogenated. That is, it does not include any fluorine, chlorine, bromine, or iodine atoms.

Specific $C_3$-$C_6$ alkyl alkanoates include, for example, methyl acetate, ethyl acetate, methyl propionate, ethyl propionate, or a combination thereof. Specific $C_2$-$C_6$ alkyl cyanides include, for example, acetonitrile, propionitrile, butyronitrile, or a combination thereof. In some embodiments, the solvent is acetone. In some embodiments, the solvent is methyl ethyl ketone. In some embodiments, the solvent is methyl isobutyl ketone. In some embodiments, the solvent is N-methyl-2-pyrrolidone. In some embodiments, the solvent is dimethylformamide. In some embodiments, the solvent is ethylene glycol monomethyl ether.

When a solvent is utilized, the curable composition can comprise 2 to 100 parts by weight of the solvent, based on 100 parts by weight total of the phenylene ether oligomer, the curing promoter, and the auxiliary resin or unsaturated monomer composition. Preferably, the solvent amount can be 5 to 80 parts by weight, more preferably 10 to 60 parts by weight, and even more preferably 20 to 40 parts by weight, based on 100 parts by weight total of the phenylene ether oligomer, the curing promoter, and any auxiliary resin. The solvent can be chosen, in part, to adjust the viscosity of the curable composition. Thus, the solvent amount can depend on variables including the type and amount of phenylene ether oligomer, the type and amount of curing promoter, the type and amount of auxiliary resin, and the processing temperature used for any subsequent processing of the curable composition, for example, impregnation of a reinforcing structure with the curable composition for the preparation of a composite/

The curable composition can further comprise an inorganic filler. Suitable inorganic fillers include, for example, alumina, silica (including fused silica and crystalline silica), boron nitride (including spherical boron nitride), aluminum nitride, silicon nitride, magnesia, magnesium silicate, glass fibers, glass mat, or a combination thereof. Suitable glass fibers include those based on E, A, C, ECR, R, S, D, and NE glasses, as well as quartz. The glass fiber can have a diameter of 2 to 30 micrometers, preferably 5 to 25 micrometers, more preferably 5 to 15 micrometers. The length of the glass fibers before compounding can be 2 to 7 millimeters, preferably 1.5 to 5 millimeters. Alternatively, longer glass fibers or continuous glass fibers can be used. The glass fiber can, optionally, include an adhesion promoter to improve its compatibility with the poly(arylene ether), the auxiliary epoxy resin, or both. Adhesion promoters include chromium complexes, silanes, titanates, zircon-aluminates, propylene maleic anhydride copolymers, reactive cellulose esters, and the like. Suitable glass fiber is commercially available from suppliers including, for example, Owens Corning, Nippon Electric Glass, PPG, and Johns Manville.

When an inorganic filler is utilized, the curable composition can comprise 2 to 900 parts by weight of inorganic filler, based on 100 parts by weight total of the poly(arylene ether), the curing promoter, and the auxiliary epoxy resin. In some embodiments, the curable composition comprises 100 to 900 parts by weight inorganic filler, preferably 200 to 800 parts by weight inorganic filler, and more preferably 300 to 700 parts by weight inorganic filler, based on 100 parts by weight total poly(arylene ether), curing promoter, and auxiliary epoxy resin. In some embodiments, the curable composition comprises less than 50 parts by weight inorganic filler, or less than 30 parts by weight inorganic filler, or less than 10 parts by weight inorganic filler, based of 100 parts by weight total of the poly(arylene ether), the curing promoter, and the auxiliary epoxy resin. In some embodiments, the curable composition can be substantially free of inorganic filler (that is, the composition can comprises less than 0.1 weight percent of added inorganic filler, based 100 parts by weight of the poly(arylene ether), the curing promoter, and the auxiliary epoxy resin).

The curable composition can, optionally, further comprise one or more additives. Suitable additives include, for example, solvents, dyes, pigments, colorants, antioxidants, heat stabilizers, light stabilizers, plasticizers, lubricants, flow modifiers, drip retardants, flame retardants, antiblocking agents, antistatic agents, flow-promoting agents, processing aids, substrate adhesion agents, mold release agents, toughening agents, low-profile additives, stress-relief additives, or a combination thereof.

The curable composition can comprise the phenylene ether oligomer described herein, a curing promoter, a solvent, and an auxiliary resin. In some embodiments, the composition is free of coreactive curing agent other than the phenylene ether oligomer.

The curable composition can comprise 1 to 99 weight percent of the auxiliary curable resin, a curable unsaturated monomer composition, or both and 1 to 99 weight percent of the phenylene ether oligomer, based on the total weight of the curable composition. For example, the composition can include 20 to 99 weight percent of the auxiliary curable resin, a curable unsaturated monomer composition, or both and 1 to 80 weight percent of the phenylene ether oligomer.

A cured composition is obtained by heating the curable composition defined herein for a time and temperature sufficient to evaporate the solvent and effect curing. For example, the curable composition can be heated to a temperature of 50 to 250° C. to cure the composition and provide the thermoset composition. The cured composition can also be referred to as a thermoset composition. In curing, a cross-linked, three-dimensional polymer network is formed. For certain thermoset resins, for example (meth)acrylate resins, curing can also take place by irradiation with actinic radiation at a sufficient wavelength and time. In some embodiments, curing the composition can include injecting the curable composition into a mold, and curing the injected composition at 150 to 250° C. in the mold.

The thermoset composition can have one or more desirable properties. For example, the thermoset composition can have a glass transition temperature of greater than or equal to 180° C., preferably greater than or equal to 190° C., more preferably greater than or equal to 200° C. The thermoset composition can also advantageously exhibit a low dielectric constant (Dk), a low dissipation factor (Df), and reduced moisture absorption. Thus, thermoset compositions comprising the phenylene ether oligomer of the present disclosure can be particularly well suited for use in electronics applications.

The curable composition described herein can also be particularly well suited for use in forming various articles. For example, useful articles can be in the form of a composite, a foam, a fiber, a layer, a coating, an encapsulant, an adhesive, a sealant, a molded component, a prepreg, a casing, a laminate, a metal clad laminate, an electronic composite, a structural composite, or a combination comprising at least one of the foregoing. In some embodiments, the article can be in the form of a composite that can be used in a variety of application, for example printed circuit boards.

A method of forming a composite comprises impregnating a reinforcing structure with the curable composition described herein; partially curing and removing at least a portion of the non-halogenated solvent from the curable composition to form a prepreg; and laminating and curing a plurality of the prepregs.

Reinforcing structures suitable for prepreg formation are known in the art.

Suitable reinforcing structures include reinforcing fabrics. Reinforcing fabrics include those having complex architectures, including two- or three-dimensional braided, knitted, woven, and filament wound. The curable composition is capable of permeating these reinforcing structures. The reinforcing structure can comprise fibers of materials known for the reinforcement of plastics, for example fibers of carbon, glass, metal, and aromatic polyamides. Suitable reinforcing structures are described, for example, in Anonymous (Hexcel Corporation), "Prepreg Technology", March 2005, Publication No. FGU 017b; Anonymous (Hexcel Corporation), "Advanced Fibre Reinforced Matrix Products for Direct Processes," June 2005, Publication No. ITA 272; and Bob Griffiths, "Farnborough Airshow Report 2006," CompositesWorld.com, September 2006. The weight and thickness of the reinforcing structure are chosen according to the intended use of the composite using criteria well known to those skilled in the production of fiber reinforced resin composites. The reinforced structure can contain various finishes compatible with the thermoset resin.

The method of forming the composite comprises partially curing the curable composition, also known as a varnish, after the reinforcing structure has been impregnated with it. Partial curing is curing sufficient to reduce or eliminate the wetness and tackiness of the curable composition yet insufficient to fully cure the composition. The thermoset resin in a prepreg is customarily partially cured. References herein to a "cured composition" refer to a composition that is fully cured. The thermoset resin in a laminate formed from prepregs is fully cured. The skilled person can readily determine whether a composition is partially cured or fully cured without undue experimentation. For example, one can analyze a sample by differential scanning calorimetry to look for an exotherm indicative of additional curing occurring during the analysis. A sample that is partially cured will exhibit an exotherm. A sample that is fully cured will exhibit little or no exotherm. Partial curing can be effected by subjecting an reinforcing structure impregnated with thermoset resin to a temperature of 133 to 140° C. for 4 to 10 minutes.

The curable compositions described herein are readily adaptable to existing commercial-scale processes and equipment. For example, prepregs are often produced on treaters. The main components of a treater include feeder rollers, a resin impregnation tank, a treater oven, and receiver rollers. The reinforcing structure (E-glass, for example) is usually rolled into a large spool. The spool is then put on the feeder rollers that turn and slowly roll out the reinforcing structure.

The reinforcing structure then moves through the resin impregnation tank, which contains the curable composition (varnish). The varnish impregnates the reinforcing structure. After emerging from the tank, the coated reinforcing structure moves upward through a vertical treater oven, which is at a temperature of 175 to 200° C., and the solvent of the varnish is boiled away. The thermoset resin begins to polymerize at this time. When the composite comes out of the tower it is sufficiently cured so that the resulting web is not wet or tacky. However curing is stopped short of completion so that additional curing can occur when the laminate is made. The web then rolls the prepreg onto a receiver roll. Thus in some embodiments, a composite is formed by impregnating a reinforcing structure with the curable composition described herein; removing at least a portion of the non-halogenated solvent from the curable composition and effecting partial cure to form a prepreg; and laminating and curing a plurality of prepregs. The composites described herein can be used for the manufacture of printed circuit boards. Thus, a printed circuit board comprises a composite formed by impregnating a reinforcing structure with the curable composition described herein; removing at least a portion of the non-halogenated solvent from the curable composition and effecting partial cure to form a prepreg; and laminating and curing a plurality of the prepregs.

This disclosure is further illustrated by the following examples, which are non-limiting.

EXAMPLES

Materials used for the following examples are described in Table 1.

(0.53 grams), and a mixture of DBEDA (0.084 gram), PTA-1 (0.045 grams), and toluene (0.15 grams) were charged to a 500 ml bubbling polymerization vessel and stirred under nitrogen. 0.40 grams catalyst solution (0.03 grams $Cu_2O$ and 0.37 grams of 48% HBr) was added to the above reaction mixture. After the addition of catalyst solution, oxygen flow was started. The temperature was ramped from 25° C. to 39.4° C. in 15 minutes, and at 70 minutes it was increased to 48.9° C. Oxygen flow was maintained for 130 minutes, at which point the flow was stopped, and 1.0 grams NTA and 6.0 grams water were added to the reaction mixture. The resulting mixture was stirred at 60° C. for 2 hours. The layers were separated by centrifugation and the light phase was isolated by removal of toluene. There observed purple colored crystals at the interface after the centrifugation which were filtered and analyzed. The oligomer was obtained after drying in a vacuum oven at 110° C. under nitrogen overnight.

PPE-CMP-2VB oligomers were synthesized according to the following procedure. CMP-PPE oligomer (25 grams) was dissolved in of xylene (50.65 grams) in a 250 ml glass reactor. To this solution, vinyl benzyl chloride (6.59 grams) and PTC-2 (0.264 grams). The jacket temperature was increase to 75° C. To this solution 3.66 grams of aqueous NaOH (50/50) solution was added slowly. The reaction mixture was stirred at 75° C. for 4 hours. After cooling down to room temperature, the mixture was neutralized with 20 ml of aqueous HCl (10%) solution. After the organic phase was separated it was washed with 20 ml aqueous HCl solution followed by 2 times wash with 20 ml deionized water. The organic phase was then separated and precipitated into methanol. The oligomer powder was obtained after drying under vacuum and nitrogen at ambient temperature.

TABLE 1

| Component | Description | CAS# | Supplier |
|---|---|---|---|
| CMP | 2-Methyl-6-cyclohexylphenol | 4855-68-9 | SI Group |
| CP | 2-Cyclohexylphenol | 119-42-6 | Sigma-Aldrich |
| TMBPA | Tetramethyl bisphenol A | 5613-46-7 | Deepak Novachem |
| $Cu_2O$ | Cuprous oxide | 1317-39-1 | American Chemet Corporation |
| HBr | Hydrobromic acid | 10035-10-6 | Chemtura Corporation |
| DBEDA | Di-tert-butylethylenediamine | 4062-60-6 | Achiewell LLC |
| DBA | Di-n-butylamine | 111-92-2 | Oxea Corporation |
| DMBA | N,N-Dimethylbutylamine | 927-62-8 | Oxea Corporation |
| PTC-1 | 50% didecyl dimethyl ammonium chloride in 50% toluene, available as MAQUAT | 7173-51-5 | Mason Chemical Company |
| NTA | Nitrilotriacetic acid trisodium salt | 5064-31-3 | Akzo Nobel Functional Chemicals LLC |
| MEK | Methyl ethyl ketone | 78-93-3 | Fisher Scientific |
| Toluene | — | 108-88-3 | Fisher Scientific |
| Chloroform | — | 67-66-3 | Fisher Scientific |
| VBC | Mixture of 3- and 4- vinylbenzyl chloride | 30030-25-2 | Sigma-Aldrich |
| NaOH | Aqueous sodium hydroxide solution (50%) | 1310-73-2 | Fisher Scientific |
| PTC-2 | Methyltri($C_8$-$C_{10}$ alkyl) ammonium chloride available as ADOGEN 464 | 72749-59-8 | Sigma-Aldrich |
| Xylenes | — | 1330-20-7 | Fisher Scientific |
| Methanol | — | 67-56-1 | Fisher Scientific |

Oxidative coupling polymerization reactions were carried out in a bubbling reactor, a 500 ml jacketed glass reactor charged with an overhead agitator, a thermocouple, nitrogen pad and a dip tube for oxygen bubbling. The derivatization or end capping reaction was carried out in a 250 ml jacketed glass reactor equipped with an overhead agitator and thermocouple.

PPE-CMP oligomers were synthesized according to the following procedure. Toluene (189.15 grams), CMP (46.9 grams), TMBPA (6.40 grams), DMBA (1.89 grams), DBA The following testing procedures were used in the following examples.

Nuclear Magnetic Resonance (NMR) Spectroscopy Analysis: The chemical structure and composition of the oligomers were determined by NMR analysis. All $^1$H NMR spectra were acquired on a Varian Mercury Plus 400 instrument operating at an observe frequency of 400.14 MHz.

Intrinsic Viscosity (IV) Measurements: IV of the oligomers was examined using an Ubbelohde capillary type viscometer and stop watch. Different concentrations of oligomers were prepared in chloroform and measurements were done at 25° C. in a thermostatted water bath. The flow time data was used to calculate the intrinsic viscosity by extrapolating the reduced viscosity to zero concentration.

Solution Viscosity Measurements: DV2+ pro Brookfield viscometer equipped with an UL adaptor for low viscosity materials. The measurements were conducted to determine the solution viscosity of the 50 wt. % oligomers in MEK using spindle 00 at 25° C. controlled by a water jacket.

Differential scanning calorimetry (DSC): The glass transition temperatures, Tg, of the oligomers were measured using a TA Instruments differential scanning calorimeter from 30° C. to 200° C. at a 10° C./min temperature ramp. The analyses were conducted under nitrogen.

All sample weights were in the range of 15.0±5 milligrams.

Example 1

PPE-CMP was prepared according to the above-described synthesis. The structure of CMP-PPE was confirmed by solution NMR spectroscopy. NMR analysis revealed that the final structure of CMP-PPE is composed of 2-methyl-6-cyclohexylphenol and TMBPA groups, which are incorporated into the backbone with an ether bond. It was also found from NMR analysis that end groups of CMP-PPE are phenolic units that results in a bi-functional oligomer with an average functionality of two.

Table 2 compares some of the important final properties of PPE-DMP and PPE-CMP. Even though PPE-CMP has a higher number average molecular weight (Mn), its solution viscosity is lower than that of PPE-DMP, which is evident from lower intrinsic viscosity and lower MEK solution viscosity results for PPE-CMP.

TABLE 2

| Property | Comparative Example (PPE-DMP) | Example 1 (PPE-CMP) |
| --- | --- | --- |
| Intrinsic Viscosity (dl/g) | 0.067 | 0.04 |
| MEK solution viscosity (cp) | 64 | 17.5 |
| Avg functionality | 2 | 2 |
| Tg (° C.) $2^{nd}$ scan | 115 | 105 |
| Absolute Mn (g/mol) | 1350 | 1550 |
| Xn | 7 | 7 |

Example 2

PPE-CMP-2VB was prepared according to the above-described synthesis, by reaction of PPE-CMP with a mixture of 3- and 4-vinylbenzyl chloride in the presence of aqueous NaOH in xylene. Final structure of isolated PPE-CMP-2VB was confirmed by solution NMR spectroscopy. In the NMR spectrum of PPE-CMP-2VB, disappearance of peaks corresponding to end group aromatic protons of PPE-CMP and formation of new peaks corresponding to vinyl benzyl group protons as well as new peaks corresponding to aromatic protons of CMP groups which are attached to vinyl benzyl end groups confirmed structure of vinyl benzyl functionalized bi-functional PPE-CMP-2VB.

Comparative Example 1

CP-PPE oligomers were synthesized according to the following procedure for comparison to the CMP-PPE oligomers described above. Toluene (168 grams), CP (49 grams), TMBPA (6.40 grams), DMBA (1.68 grams), DBA (0.56 grams), and a mixture of 0.088 grams DBEDA, 0.047 grams PTC-1, and 0.15 grams toluene were charged to a 500 milliliter bubbling polymerization vessel and stirred under nitrogen. Catalyst solution (0.42 grams; 0.03 grams $Cu_2O$ and 0.39 grams (48%) HBr) was added to the above reaction mixture. After the addition of catalyst solution, oxygen flow was started. The temperature was ramped from 25° C. to 39.4° C. in 15 minutes, and at 70 minutes it was increased to 48.9° C. Oxygen flow was maintained for 130 minutes, at which point the flow was stopped, and 1.0 grams NTA and 6.0 grams water were added to the reaction mixture. The resulting mixture was stirred at 60° C. for 2 hours. The layers were separated by centrifugation and the light phase was isolated by precipitation into methanol. The precipitated particles were filtered and analyzed after drying in a vacuum oven at 110° C. under nitrogen overnight.

The CP-PPE oligomers were characterized by $^1H$ and $^{31}P$ NMR spectroscopy. All $^1H$ NMR spectra were acquired on an Agilent DD2 600 instrument operating at an observe frequency of 599.90 MHz. Spectra for all samples were collected under quantitative conditions. Approximately 30 mg 2-cyloheyl phenol final ppt sample were added to 1 milliliter 1,1,2,2-tetrachloroethane-$d_2$. Spectral parameters included an 9615 Hz spectral width, 1.7s acquisition time (16 K data points), 4.20 μs pulse width (45° flip angle), and 15 s pulse delay. The s2pul pulse sequence was employed. Typically, 32 acquisitions were adequate to achieve good signal-to-noise. Data processing was carried out using NetNMR software with 0.25 Hz line broadening and a polynomial baseline correction routine.

$^{31}P$-NMR spectroscopy was used for the identification and quantification of phenolic functionality in various polymer samples. This technique involves the derivatization of the polymer phenolic residues with 2-chloro-1,3,2-dioxaphospholane. This reaction produces a variety of structurally similar 2-aryloxy-1,3,2-dioxaphospholanes differing only in aromatic ring substitution. Because of the sensitivity of the $^{31}P$-nucleus to its electronic environment, various phenolic endgroups can be identified from $^{31}P$-chemical shifts of their corresponding phosphate derivatives. In addition to phenolic endgroups, this method can also quantify alcohol and acidic functionalities in many resins. Through the use of the internal standard, 2,4-dibromophenol, quantification of the hydroxyl end-group functionality of polymeric resins can be determined.

All spectra were acquired on an Agilent DD2 600 spectrometer operating at 242.84 MHz for $^{31}P$. The instrument was equipped with a 5 mm OneNMR™ PFG probe. Approximately 80 mg of sample were dissolved in 4.0 ml of chloroform-d containing 0.95 mg/ml 2,4-dibromophenol (internal standard) and 15 mg/ml Cr(acac)$_3$ (Ti relaxation enhancement reagent to reduce data acquisition times). In addition, pyridine is added as an acid scavenger at 1 ml pyridine per 100 ml CDCl$_3$ internal standard stock solution. Record sample and internal standard weights to four decimal places. The decoupler was gated off during the pulse delay to eliminate NOE and to ensure complete relaxation of phosphorus nuclei between scans. Acquisition parameters included a pulse delay of 3s and a 45° flip angle. Also, a 23.6 kHz spectral width (100 to 200 ppm region) and 32 K data points resulted in a 1.39s acquisition time. Typically, 1024 scans were required for adequate signal-to-noise. Broadband proton decoupling was carried out using the Waltz-16 pulse sequence. The internal standard, 2,4-dibromo-phenol signal was used as a chemical shift reference (δ=130.24 ppm). Resulting spectra were processed using 1 Hz exponential apodization and were baseline corrected using a polynomial fit routine. All data processing was done using NetNMR software.

The cyclohexyl phenol and tetramethyl bisphenol A copolymer (CP-PPE) was synthesized by oxidative coupling polymerization, as described above. The material was precipitated to remove unreacted monomers for better structure analysis. NMR spectroscopy was used to determine the chemical structure. The residual amount of monomer was determined by $^{31}$P NMR. The branching at unsubstituted 6-position was confirmed via $^1$H NMR spectroscopy based on the number of protons in the aromatic ring. If linear polymers were obtained the number of protons should be 3 however, it was determined as 2.5. Thus the CP-PPE oligomers exhibited a branched structure.

This disclosure further encompasses the following aspects.

Aspect 1: A phenylene ether oligomer comprising repeating units of the structure

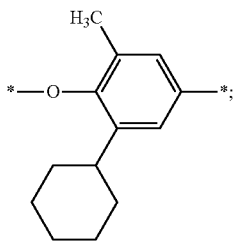

wherein the phenylene ether oligomer comprises less than 30 weight percent of repeating units derived from a monohydric phenol having identical substituents in the 2- and 6-positions; and wherein the phenylene ether oligomer comprises a vinyl benzene ether end group, an amine end group, maleimide end group, norbornene group, an anhydride group, or a combination comprising at least one of the foregoing.

Aspect 2: The phenylene ether oligomer of aspect 1, wherein the phenylene ether oligomer has a number average molecular weight of 600 to 5,000 grams per mole, determined by gel permeation chromatography relative to polystyrene standards.

Aspect 3: The phenylene ether oligomer of aspect 1 or 2, wherein the phenylene ether oligomer has an intrinsic viscosity of less than 0.15 deciliter per gram, measured by Ubbelohde viscometer at 25° C. in chloroform.

Aspect 4: The phenylene ether oligomer of any one or more of aspects 1 to 3, wherein the phenylene ether oligomer comprises a vinyl benzene ether end group.

Aspect 5: The phenylene ether oligomer of any one or more of aspects 1 to 4, wherein the phenylene ether oligomer is of the structure

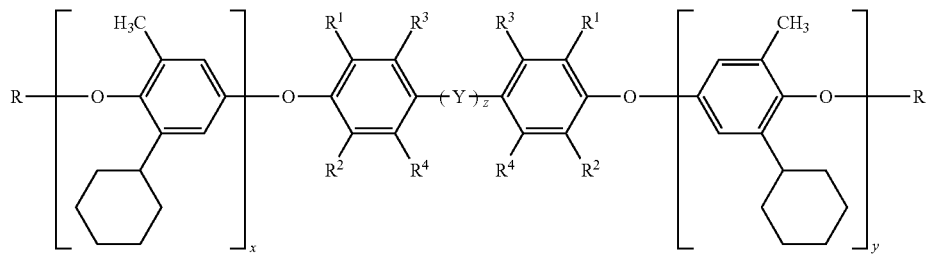

wherein x and y are independently 0 to 30, provided that the sum of x and y is at least 2; each occurrence of $R^1$, $R^2$, $R^3$, and $R^4$ independently comprises hydrogen, halogen, unsubstituted or substituted $C_1$-$C_{12}$ primary or secondary hydrocarbyl, $C_1$-$C_{12}$ hydrocarbylthio, $C_1$-$C_{12}$ hydrocarbyloxy, or $C_2$-$C_{12}$ halohydrocarbyloxy wherein at least two carbon atoms separate the halogen and oxygen atoms; z is 0 or 1; Y has a structure comprising

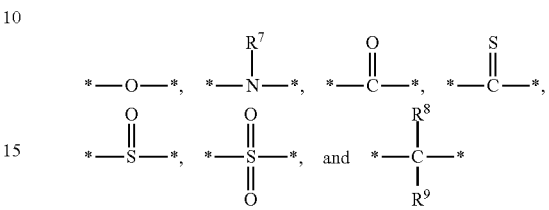

wherein each occurrence of $R^7$ independently comprises hydrogen and $C_1$-$C_{12}$ hydrocarbyl, and each occurrence of $R^8$ and $R^9$ is each independently hydrogen, $C_1$-$C_{12}$ hydrocarbyl, or $C_1$-$C_6$ hydrocarbylene wherein $R^8$ and $R^9$ collectively form a $C_4$-$C_{12}$ alkylene group; and R is independently at each occurrence a vinyl benzene ether end group, an amine end group, or a maleimide end group.

Aspect 6: The phenylene ether oligomer of aspect 5, wherein each occurrence of $R^1$ and $R^2$ is methyl, each occurrence of $R^3$ and $R^4$ is hydrogen, Y is an isopropylidene group, and R is a vinyl benzyl ether group.

Aspect 7: The phenylene ether oligomer of any one or more of aspects 1 to 4, wherein the phenylene ether oligomer comprises a polysiloxane block.

Aspect 8: A method of making the phenylene ether oligomer of any one or more of aspects 1 to 7, the method comprising oxidatively polymerizing 2-methyl-6-cyclohexyl phenol in the presence of a catalyst to provide the phenylene ether oligomer.

Aspect 9: The method of aspect 8, further comprising reacting the phenylene ether oligomer with a vinyl benzene ether group, an amine group, a maleimide group, a norbornene group, an anhydride group, or a combination comprising at least one of the foregoing to provide a functionalized phenylene ether oligomer.

Aspect 10: A curable composition comprising the phenylene ether oligomer of any one or more of aspects 1 to 7; and a curing promoter.

Aspect 11: The curable composition of aspect 10, wherein the curing promoter comprises an amine, a dicyandiamide, a polyamide, an amidoamine, a Mannich base, an anhydride, a phenol-formaldehyde resin, a carboxylic acid functional polyester, a polysulfide, a polymercaptan, an isocyanate, a cyanate ester, or combinations thereof.

Aspect 12: The curable composition of aspect 10 or 11, further comprising an auxiliary curable resin, a curable unsaturated monomer composition, or both, preferably wherein the auxiliary curable resin comprises an epoxy resin, a cyanate ester resin, a maleimide resin, a benzoxazine resin, a vinylbenzyl ether resin, an arylcyclobutene resin, a perfluorovinyl ether resin, oligomers or polymers with curable vinyl functionality, or a combination thereof, and the curable unsaturated monomer composition comprises a monofunctional styrenic compound, a monofunctional (meth)acrylic compound, a polyfunctional allylic compound, a polyfunctional (meth)acrylate, a polyfunctional (meth)acrylamide, a polyfunctional styrenic compound, or a combination thereof.

Aspect 13: A thermoset composition comprising a cured product of the curable composition of any one or more of aspects 10 to 12, preferably wherein the thermoset composition has a glass transition temperature of greater than or equal to 180° C., preferably greater than or equal to 190° C., more preferably greater than or equal to 200° C.

Aspect 14: An article comprising the thermoset composition of aspect 13, preferably wherein the article is in the form of a composite, a foam, a fiber, a layer, a coating, an encapsulant, an adhesive, a sealant, a molded component, a prepreg, a casing, a laminate, a metal clad laminate, an electronic composite, a structural composite, or a combination comprising at least one of the foregoing.

Aspect 15: A method for the manufacture of a thermoset composition, the method comprising curing the curable composition of aspects 10 to 12, preferably at a temperature of 50 to 250° C.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other. "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some embodiments," "an embodiment," and so forth, means that a particular element described in connection with the embodiment is included in at least one embodiment described herein, and may or may not be present in other embodiments. In addition, it is to be understood that the described elements may be combined in any suitable manner in the various embodiments.

Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

Compounds are described using standard nomenclature. For example, any position not substituted by any indicated group is understood to have its valency filled by a bond as indicated, or a hydrogen atom. A dash ("-*") that is not between two letters or symbols is used to indicate a point of attachment for a substituent. For example, *—CHO is attached through the carbon of the carbonyl group.

As used herein, the term "hydrocarbyl," whether used by itself, or as a prefix, suffix, or fragment of another term, refers to a residue that contains only carbon and hydrogen. The residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. However, when the hydrocarbyl residue is described as substituted, it may, optionally, contain heteroatoms over and above the carbon and hydrogen members of the substituent residue. Thus, when specifically described as substituted, the hydrocarbyl residue can also contain one or more carbonyl groups, amino groups, hydroxyl groups, or the like, or it can contain heteroatoms within the backbone of the hydrocarbyl residue. The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. "Arylene" means a divalent aryl group. "Alkylarylene" means an arylene group substituted with an alkyl group. "Arylalkylene" means an alkylene group substituted with an aryl group (e.g., benzyl). The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, Si, or P. "Substituted" means that the compound or group is substituted with at least one (e.g., 1, 2, 3, or 4) substituents that can each independently be a C$_{1-9}$ alkoxy, a C$_{1-9}$ haloalkoxy, a nitro (—NO$_2$), a cyano (*—CN), a C$_1$-6 alkyl sulfonyl (*—S(=O)$_2$-alkyl), a C$_{6-12}$ aryl sulfonyl (*—S(=O)$_2$-aryl)a thiol (*—SH), a thiocyano (*—SCN), a tosyl (CH$_3$C$_6$H$_4$SO$_2$—*), a C$_{3-12}$ cycloalkyl, a C$_{2-12}$ alkenyl, a C$_{5-12}$ cycloalkenyl, a C$_{6-12}$ aryl, a C$_{7-13}$ arylalkylene, a C$_{4-12}$ heterocycloalkyl, and a C$_{3-12}$ heteroaryl instead of hydrogen, provided that the substituted atom's normal valence is not exceeded. The number of carbon atoms indicated in a group is exclusive of any substituents. For example *—CH$_2$CH$_2$CN is a C$_2$ alkyl group substituted with a nitrile.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A phenylene ether oligomer comprising repeating units of the structure wherein the phenylene ether oligomer comprises less than 0.1 weight percent of repeating units derived from a monohydric phenol having identical substituents in the 2- and 6-positions; and wherein the phenylene ether oligomer comprises a vinyl benzene ether end group, an amine end group, maleimide end group, a norbornene group, an anhydride group, or a combination comprising at least one of the foregoing.

2. The phenylene ether oligomer of claim 1, wherein the phenylene ether oligomer has a number average molecular weight of 600 to 5,000 grams per mole, determined by gel permeation chromatography relative to polystyrene standards.

3. The phenylene ether oligomer of claim 1, wherein the phenylene ether oligomer has an intrinsic viscosity of less than 0.15 deciliter per gram, measured by Ubbelohde viscometer at 25° C. in chloroform.

4. The phenylene ether oligomer of claim 1, wherein the phenylene ether oligomer comprises a vinyl benzene ether end group.

5. The phenylene ether oligomer of claim 1, wherein the phenylene ether oligomer is of the structure wherein x and y are independently 0 to 30, provided that the sum of x and y is at least 2;

each occurrence of R$^1$, R$^2$, R$^3$, and R$^4$ independently comprises hydrogen, halogen, unsubstituted or substituted C$_1$-C$_{12}$ primary or secondary hydrocarbyl, C$_1$-C$_{12}$ hydrocarbylthio, C$_1$-C$_{12}$ hydrocarbyloxy, or C$_2$-C$_{12}$ halohydrocarbyloxy wherein at least two carbon atoms separate the halogen and oxygen atoms;

z is 0 or 1;

Y has a structure comprising wherein each occurrence of R$^7$ independently comprises hydrogen and C$_1$-C$_{12}$ hydrocarbyl, and each occurrence of R$^8$ and R$^9$ is each independently hydrogen, C$_1$-C$_{12}$ hydrocarbyl, or C$_1$-C$_6$ hydrocarbylene wherein R$^8$ and R$^9$ collectively form a C$_4$-C$_{12}$ alkylene group; and R is independently at each occurrence a vinyl benzene ether end group, an amine end group, or a maleimide end group, a norbornene end group, or an anhydride group.

6. The phenylene ether oligomer of claim 5, wherein each occurrence of R$^1$ and R$^2$ is methyl, each occurrence of R$^3$ and R$^4$ is hydrogen, Y is an isopropylidene group, and R is a vinyl benzyl ether group.

7. The phenylene ether oligomer of claim 1, wherein the phenylene ether oligomer comprises a polysiloxane block.

8. A method of making the phenylene ether oligomer of claim 1, the method comprising oxidatively polymerizing 2-methyl-6-cyclohexyl phenol in the presence of a catalyst to provide the phenylene ether oligomer.

9. The method of claim 8, further comprising reacting the phenylene ether oligomer with a vinyl benzene ether group, an amine group, a maleimide group, a norbornene group, an anhydride group, or a combination comprising at least one of the foregoing to provide a functionalized phenylene ether oligomer.

10. A curable composition comprising the phenylene ether oligomer of claim 1; and a curing promoter.

11. The curable composition of claim 10, wherein the curing promoter comprises an amine, a dicyandiamide, a polyamide, an amidoamine, a Mannich base, an anhydride, a phenol-formaldehyde resin, a carboxylic acid functional polyester, a polysulfide, a polymercaptan, an isocyanate, a cyanate ester, or combinations thereof.

12. The curable composition of claim 10, further comprising an auxiliary curable resin, a curable unsaturated monomer composition, or both.

13. A thermoset composition comprising a cured product of the curable composition of claim 10.

14. An article comprising the thermoset composition of claim 13.

15. A method for the manufacture of a thermoset composition, the method comprising curing the curable composition of claim 10.

* * * * *